(12) United States Patent
Wu et al.

(10) Patent No.: US 7,253,291 B2
(45) Date of Patent: Aug. 7, 2007

(54) PROCESSES FOR THE PREPARATION OF N-SUBSTITUTED PHTHALIMIDES

(75) Inventors: Yanzhong Wu, Bronx, NY (US); Panolil Raveendranath, Monroe, NY (US)

(73) Assignee: Wyeth, Madison, NJ (US)

( * ) Notice: Subject to any disclaimer, the term of this patent is extended or adjusted under 35 U.S.C. 154(b) by 22 days.

(21) Appl. No.: 10/989,840

(22) Filed: Nov. 16, 2004

(65) Prior Publication Data

US 2005/0107618 A1    May 19, 2005

Related U.S. Application Data

(60) Provisional application No. 60/520,757, filed on Nov. 17, 2003.

(51) Int. Cl.
*C07D 209/48* (2006.01)
(52) U.S. Cl. .................................... 548/473
(58) Field of Classification Search ............... 548/473
See application file for complete search history.

(56) References Cited

U.S. PATENT DOCUMENTS 3,402,179 A    9/1968    Fujimoto et al.
6,989,401 B2 *  1/2006    Maeda et al. ............... 514/418

FOREIGN PATENT DOCUMENTS

NL        6501131        8/1965
NL        6600916        7/1966
WO    WO 03/048122 A2    6/2003

OTHER PUBLICATIONS

Mitsunobu et al., "Stereospecific and Stereoselective Reactions. I. Preparation of Amines from Alcohols," J. Am. Chem. Soc., vol. 94., Iss. 2, pp. 679-680 (1972).*
The Merck Index, 12th Ed. Budvari et al., p. 9350 & 9666 (1996).*
Mitsunobu et al., "Stereospecific and Stereoselective Reactions. I. Preparation of Amines from Alcohols," J. Am. Chem. Soc., vol. 94, Iss. 2, pp. 679-680 (1972).*
Griffiths, Jonathan, Tetrahedron, 1992, 48, 26, 5543-5556.
Jackson, et al., Aust. J. Chem., 1988, 41, 8, 1201-1208.
Sevensson, et al., Acta Pharm. Suec., 1975, 12(3), 290-2.
Jackson, et al., Tetrahedron Lett., 1988; 29, 16, 1983-1984.
Hoffman, et al., J. Med. Chem., 1975; 18, 278-284.
Iyer, et al., J. Am. Chem. Soc., 1987, 109, 9, 2759-2770.
Gibson, et al., Angew. Chem. Int. Ed. Engl., 1968, 7, 919.
Ing, et al., J. Chem. Soc., 1926, 2348.
Mitsunobu, et al., Bull. Chem. Soc. Jpn., 1967, 40, 2380.
Camp, et al., Aust. J. Chem., 1988, 41, 1835.
Bouix C. et al., "Stereoselective Synthesis of Arabinose-derived Phosphonates," *Tetrahedron Letters* (1998) 39(8):825-828.
Fokina N. et al., "Towards optically pure mono- and difluorinated amino acids," *Synthesis* (2002) 17:2589-2596.
Mitsunobu O. "The use of diethyl azodicarboxylate and triphenylphosphine in synthesis and transformation of natural products," *Synthesis* (Jan. 1981) 1-28.
Ramesh N.G. et al., "Mitsunobo Reaction of 1,5-Anhydro-3, 4, 6-tri-O-benzyl-2-deoxy-2-hydroxymethyl-hex-1-enitols and 1,5-Anhydro-2-deoxy-4, 6-O-protected-hex-1- enitols. A Novel Method for the Synthesis of 2-C-Methylene Glycosides and an Useful Alternative to Ferrier Rearrangement," *Tetrahedron* (1995) 51(1):255-272.
Wada et al., "Stereospecific and stereoselective reactions. II. Preparation of esters of N-phthaloyl-α-amino acid from esters of α-hydroxy acid," *Bulletin of the Chemical Society of Japan* (1973) 46:2833-2835.
International Search Report dated Apr. 14, 2005 for International Application No. PCT/US2004/038335.

* cited by examiner

*Primary Examiner*—Golam Shameem
*Assistant Examiner*—Andrew B. Freistein
(74) *Attorney, Agent, or Firm*—Fish & Richardson P.C.

(57) ABSTRACT

The present invention describes a process for preparing N-substituted phthalimides of Formula I which are widely useful as intermediates in the preparation of organic compounds such as pharmaceuticals

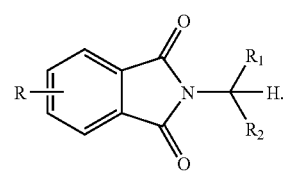

I

22 Claims, No Drawings

PROCESSES FOR THE PREPARATION OF N-SUBSTITUTED PHTHALIMIDES

CROSS-REFERENCE TO RELATED APPLICATIONS

This application claims priority benefit of U.S. provisional application Ser. No. 60/520,757 filed Nov. 17, 2003, which is incorporated herein by reference in its entirety.

FIELD OF THE INVENTION

The present invention relates to processes for the preparation of N-substituted phthalimides.

BACKGROUND OF THE INVENTION

N-Substituted phthalimides are useful intermediates for the synthesis of a large variety of primary amines via well-known processes such as the Gabriel synthesis (e.g., Gibson et al., *Angew. Chem. Int. Ed. Engl.*, 1968, 7, 919) and Ing-Manske procedure (Ing et al., *J. Chem. Soc.*, 1926, 2348).

N-Substitution of phthalimides can be mediated by the versatile Mitsunobu reaction (Mitsunobu et al., *Bull. Chem. Soc. Jpn.*, 1967, 40, 2380; Camp et al., *Aust. J. Chem.*, 1988, 41, 1835) the general outline of which is shown below in Scheme I. This reaction typically utilizes a triarylphosphine and a dialkyl azodicarboxylate as reactants, which serve to activate a primary or secondary alcohol towards nucleophilic attack by acidic or weakly acid groups such as phenols, carboxylic acids, diimides, etc. While the Mitsunobu reaction is a versatile synthetic tool since it allows one to directly activate and substitute an alcohol group in one step, it has the drawback of generating the undesirable by-products of triphenylphosphine oxide and a dialkyl, diacyl hydrazide in stoichiometric amounts. These reaction by-products, in addition to any unreacted reagents can often lead to difficult or tedious separations, thus potentially limiting the industrial utility of the process.

Scheme I

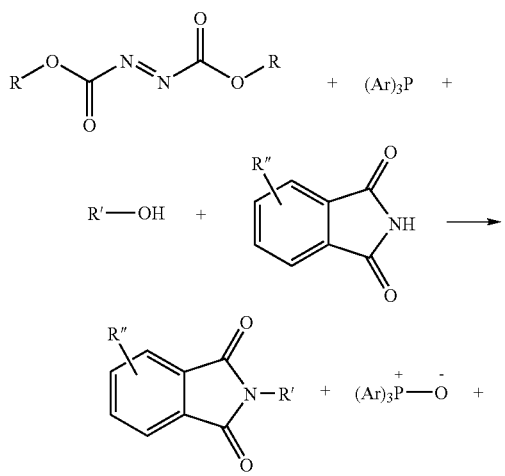

-continued

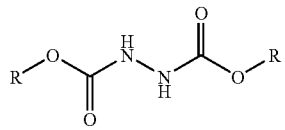

As can be well appreciated by the skilled artisan, the N-substituted phthalimides are widely useful in all areas of synthetic chemistry and particularly pharmaceutical research. For example, 2-(3-butynyl)-1-H-isoindole-1,3-(2H)-dione is used in the preparation of pain relieving drugs that are inhibitors of the enzyme cytosolic phospholipase A2 as reported in, for example WO 03/048122A2. Preparations of this intermediate via Mitsunobu and other reactions have also been reported in Griffiths et al., *Tetrahedron*, 1992, 48, 5543; Jackson et al., *Aust. J. Chem.*, 1988, 41, 1201; *Acta. Pharm. Suec.*, 1975, 12, 290; Jackson et al., *Tetrahedron*, 1988, 29, 1983; Hoffmann et al., *J. Med. Chem.*, 1975, 18, 278; NL 6600916; NL 6501131; and Iyer et al., *J. Am. Chem. Soc.*, 1987, 109, 2759. These preparations, however, tend to involve multistep syntheses, commercially unavailable starting materials, lengthy reaction times, chlorinated solvent, and/or complicated isolation or purification steps. Accordingly, improved synthetic routes to N-substituted phthalimides are needed, and the processes described herein help meet this and other needs.

SUMMARY OF THE INVENTION

The present invention provides a process for preparing a compound of Formula I:

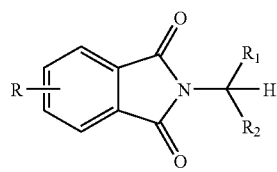

wherein:

R is hydrogen, $C_{1-2}$ alkyl, halogen, or $C_{1-2}$ alkoxy;

$R_1$ is hydrogen, $C_{1-6}$ alkyl, $C_{2-6}$ alkenyl, or $C_{2-6}$ alkynyl; and $R_2$ is $C_{1-6}$ alkyl, $C_{2-6}$ alkenyl, or $C_{2-6}$ alkynyl;

comprising reacting a compound of Formula II:

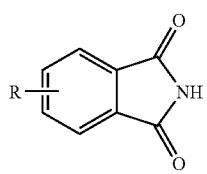

with a compound of Formula III:

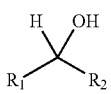

in the presence of a diazodicarboxylate having Formula IV:

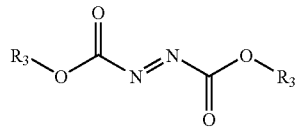

wherein each $R_3$ is, independently, $C_{1-6}$ alkyl;

and in the presence of a triarylphosphine of Formula V:

    V wherein each Ar is phenyl optionally substituted with 1-3 substituents independently selected from $CH_3$, $OCH_3$, and halogen;

and in the presence of solvent having Formula VI:

    VI wherein Ar' is phenyl optionally substituted with 1, 2, or 3 methyl groups; for a time and under conditions suitable for forming said compound of Formula I.

In some embodiments, R is hydrogen, $C_{1-2}$ alkyl, halogen, or $C_{1-2}$ alkoxy; $R_1$ is hydrogen; and $R_2$ is $C_{1-6}$ alkyl, $C_{2-6}$ alkenyl, or $C_{2-6}$ alkynyl.

In further embodiments, R is hydrogen, $C_{1-2}$ alkyl, halogen, or $C_{1-2}$ alkoxy; $R_1$ is hydrogen; and $R_2$ is $C_{2-6}$ alkenyl, or $C_{2-6}$ alkynyl.

In further embodiments, R is hydrogen; $R_1$ is hydrogen; and $R_2$ is $C_{2-6}$ alkenyl or $C_{2-6}$ alkynyl.

In yet further embodiments, R is hydrogen; $R_1$ is hydrogen; and $R_2$ is propynyl.

In some embodiments, the compound of Formula I has the Formula:

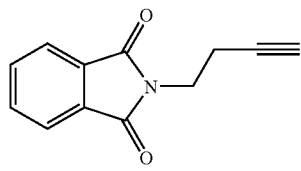

According to some embodiments, the triarylphosphine of Formula V is triphenylphosphine.

According to further embodiments, $R_3$ is methyl, ethyl, propyl, for example 2-propyl.

According to further embodiments, the solvent of Formula VI is toluene.

In yet further embodiments, the diazodicarboxylate of Formula IV is added to a mixture of compounds of Formulas II, III, V, and VI. The mixture can be maintained at a temperature of about −10 to about 30° C., and in some embodiments of about −10 to about 10° C., during the addition. In some embodiments, the diazodicarboxylate of Formula IV is added to a mixture of compounds of Formulas II, III, V, and VI at a rate such that the reaction temperature is maintained at or below room temperature.

In some embodiments, the processes described herein include precipitating the compound of Formula I from the reaction mixture, which can be induced by the addition of alcohol to the reaction mixture. Such alcohols can include alkanols having 1-10 carbon atoms, e.g., methanol, ethanol, $C_3$-alkanol, $C_4$-alkanol, $C_5$-alkanol, $C_6$-alkanol, $C_7$-alkanol, $C_8$-alkanol, $C_9$-alkanol, $C_{10}$-alkanol or combinations thereof. In some embodiments the alcohol comprises methanol. Preferably, the volume ratio of alcohol to solvent is from about 1:1 to about 1:2.

According to some embodiments, the compound of Formula I is isolated by filtration and has a purity of greater than about 95%. Preferably, the compound of Formula I is isolated by filtration in a yield greater than about 70% by weight based on the amount of compound of Formula II.

In yet further embodiments, the compound of Formula I is isolated by filtration in a yield greater than about 70% by weight based on the amount of said compound of Formula II and with a purity of greater than about 95% without the use of additional distillation, extraction, or chromatographic techniques.

DETAILED DESCRIPTION OF THE INVENTION

The present invention provides, inter alia, processes for preparing N-substituted phthalimides starting with primary or secondary alcohols. The processes described herein allow for the isolation of substantially pure N-substituted phthalimides without recourse to distillative or chromatographic methods of purification.

A general outline of the processes of the present invention is provided in Scheme II, where constituent members of the depicted compounds of Formulas I, II, III, IV, V, and VI are defined hereinabove.

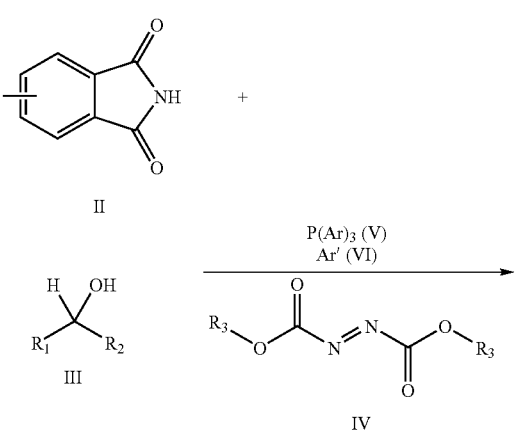

Scheme II

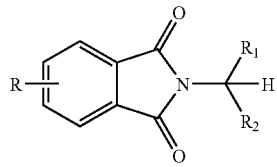

I

The preparation of N-substituted phthalimides according to the processes of the present invention can be, for example, carried out by combining in a single vessel the compounds of Formulas II, III, IV, V, and VI. Typically, the diazodicarboxylate of Formula IV is the final component to be added such that diazodicarboxylate is added to mixture of compounds of Formulas II, III, V, and VI. The addition can be conducted at reduced temperature. For example, the mixture of compounds of Formulas II, III, V, and VI can be cooled prior to addition of the diazodicarboxylate. Suitable temperatures to which the mixture can be cooled include about −20 to about 15° C., preferably about −10 to about 10° C., and more preferably about 0 to about 5° C. Addition of the diazodicarboxylate can result in an exothermic reaction and heating of the reaction mixture. The rate of addition can be regulated so that the reaction mixture temperature does not rise above a certain threshold temperature, such as about room temperature. For example, the rate of addition can be controlled so that the reaction mixture temperature is maintained at about 0 to about 30° C., preferably about 10 to about 25° C., or more preferably about 15 to about 25° C. After addition of the diazodicarboxylate, the reaction can be carried out for an additional amount of time to achieve completion. For example, the reaction mixture can be stirred for an additional 30 to 90 minutes, or about 60 minutes, at any suitable temperature such as about 10 to about 30° C., about 15 to about 25° C., or about room temperature.

Isolation of the compound of Formula I from the reaction mixture can be carried out without the use of distillation, extraction, or chromatographic techniques. For example, the compound of Formula I can be directly precipitated in good yield and purity from the reaction mixture. Precipitation can be induced by the addition of an adequate amount of solvent in which the compound of Formula I is poorly soluble. For example, addition of a sufficient amount of an alcohol can induce precipitation yet allow the reaction by-products to remain in solution for ease of separation. Suitable alcohols include methanol, ethanol, n-propanol, isopropanol, t-butanol, and the like. A combination of alcohols can also be used. Yields, by weight, of greater than about 50%, about 60%, about 70%, and about 80% can be obtained in this manner, and purity greater than about 80%, about 85%, about 90%, about 95%, about 98%, and about 99% can be obtained without further purification steps.

The processes of the present invention are advantageous for numerous reasons apparent to the skilled artisan. For example, conducting the reaction in an aromatic solvent (Ar') and subsequent addition of alcohol results in precipitation of the product from the reaction mixture while allowing the unwanted by-products and excess reagents to remain in solution, thus facilitating purification. Further, the use of common halogenated Mitsunobu solvents such as methylene chloride or chloroform, which can present waste treatment difficulties, or the use of certain ether solvents which can form potentially dangerous organic peroxides is avoided.

As used herein, the term "alkyl" or "alkylene" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, butenyl, pentenyl, hexenyl, butadienyl, pentadienyl, hexadienyl, and the like.

As used herein, "alkynyl" refers to an alkyl group having one or more triple carbon-carbon bonds. Example alkynyl groups include ethynyl, propynyl, butynyl, pentynyl, and the like.

As used herein, "halo" or "halogen" refers to fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, the term "reacting" refers to the bringing together of designated chemical reactants such that a chemical transformation takes place generating a compound different from any initially introduced into the system. Reacting can take place in the presence or absence of solvent.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, $C_6$ alkyl.

The compounds of the present invention can contain an asymmetric atom, and some of the compounds can contain one or more asymmetric atoms or centers, which can thus give rise to optical isomers (enantiomers) and diastereomers. The present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The processes described herein can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatograpy (HPLC) or thin layer chromatography.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. Solvents that are suitable according to the present invention are solvents of Formula VI including benzene and toluene.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions are typically carried out at reduced temperatures); and the kinetics of the reaction (e.g., a high activation energy barrier typically necessitates elevated temperatures). "Elevated temperature" refers to temperatures above room temperature (about 20° C.) and "reduced temperature" refers to temperatures below room temperature.

The reactions of the processes described herein can be carried out in air or under an inert atomosphere. Typically, reactions containing reagents or products that are substantially reactive with air can be carried out using air-sensitive synthetic techniques that are well known to the skilled artisan.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The processes of this invention are suitable for the preparation of compounds Formula I on any convenient scale, for example greater than about 0.01 mg, 0.10 mg, 1 mg, 10 mg, 100 mg, 1 g, 10 g, 100 g, 1 kg, 10 kg or more. The processes are particularly advantageous for the large scale (e.g., greater than about ten gram) preparation of compounds of Formula I.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLE

Preparation of 2-but-3-ynyl-isoindole-1,3-dione

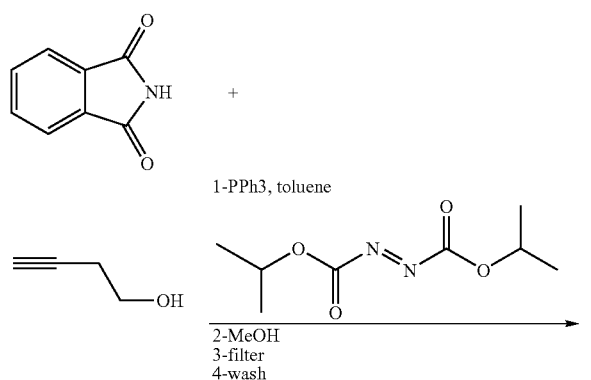

-continued

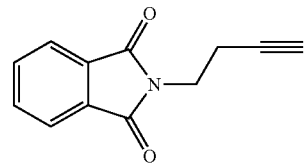

Diisopropyl azodicarboxylate (316 g, 1.56 mol) was added to a solution of triphenylphosphine (PPh$_3$) (393 g, 1.50 mol), 3-butyn-1-ol (105 g, 1.50 mol) and phthalimide (200 g, 1.36 mol) in toluene (1600 mL) which was pre-cooled with a −5° C. cooling bath at such a rate that temperature of the reaction mixture was kept between 15-25° C. The addition time was 50 min. The cooling bath was removed after the addition was finished. The reaction mixture was allowed to warm to 15-25° C. and stirred for 1 h. Then methanol (800 mL) was added. The mixture was stirred for 30 min and then filtered. The crude product was washed with methanol and dried to give a white solid (218 g) in 80% yield 99.8% purity by area. $^1$H NMR (DMSO-d$_6$): δ 7.88 (m, 4 H), 3.72 (t, 2 H, J=7.0 Hz), 2.83 (t, 1 H, J=2.7 Hz), 2.55 (m, 2 H).

As those skilled in the art will appreciate, numerous changes and modifications may be made to the preferred embodiments of the invention without departing from the spirit of the invention. It is intended that all such variations fall within the scope of the invention. It is intended that each of the patents, applications, and printed publications including books mentioned in this patent document be hereby incorporated by reference in their entirety.

What is claimed is:

1. A process for preparing a compound of Formula I:

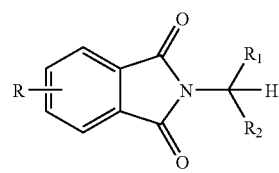

wherein:
R is hydrogen, C$_{1-2}$ alkyl, halogen, or C$_{1-2}$ alkoxy;
R$_1$ is hydrogen, C$_{1-6}$ alkyl, C$_{2-6}$ alkenyl, or C$_{2-6}$ alkynyl; and
R$_2$ is C$_{1-6}$ alkyl, C$_{2-6}$ alkenyl, or C$_{2-6}$ alkynyl;
comprising a) reacting a compound of Formula II:

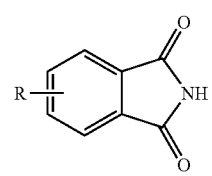

wherein R is as defined above, with a compound of Formula III:

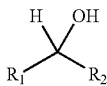
III wherein $R_1$ and $R_2$ are as defined above,
in the presence of a diazodicarboxylate having Formula IV:

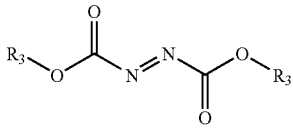
IV wherein each $R_3$ is, independently, $C_{1-6}$ alkyl;
and in the presence of a triarylphosphine of Formula V:

V wherein each Ar is phenyl optionally substituted with 1-3 substituents independently selected from $CH_3$, $OCH_3$ and halogen;
and in the presence of a solvent having Formula VI:

VI wherein Ar' is phenyl optionally substituted with 1, 2 or 3 methyl groups; to form said compound of Formula I; and b) precipitating said compound of Formula I from the reaction mixture by adding one or more alcohols to the reaction mixture, after said reacting of step a).

2. The process of claim 1 wherein $R_1$ is hydrogen.

3. The process of claim 1 wherein $R_1$ is hydrogen, and $R_2$ is $C_{2-6}$ alkenyl or $C_{2-6}$ alkynyl.

4. The process of claim 1 wherein R is hydrogen, $R_1$ is hydrogen, and $R_2$ is $C_{2-6}$ alkenyl or $C_{2-6}$ alkynyl.

5. The process of claim 1 wherein R is hydrogen, $R_1$ is hydrogen, and $R_2$ is propynyl.

6. The process of claim 1 wherein said compound of Formula I has the Formula:

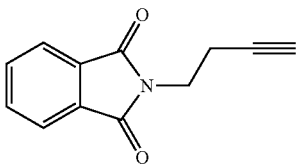

7. The process of claim 1 wherein said triarylphosphine of Formula V is triphenylphosphine.

8. The process of claim 1 wherein each $R_3$ is independently selected from the group consisting of methyl, ethyl, n-propyl and 2-propyl.

9. The process of claim 1 wherein each $R_3$ is n-propyl.

10. The process of claim 1 wherein each $R_3$ is 2-propyl.

11. The process of claim 1 wherein said solvent of Formula VI is toluene.

12. The process of claim 1 wherein said diazodicarboxylate of Formula IV is added to a mixture of compounds of Formulas II, III, V, and VI.

13. The process of claim 12 wherein said diazodicarboxylate of Formula IV is added to said mixture of compounds of Formulas II, III, V, and VI at a rate such that the reaction temperature is maintained at about −10° C. to about 30° C.

14. The process of claim 13 wherein said mixture is maintained at a temperature of about −10° C. to about 10° C. throughout the duration of said diazodicarboxylate addition.

15. The process of claim 1 wherein said one or more alcohols comprises methanol, ethanol, isopropanol, or a combination thereof.

16. The process of claim 1 wherein said one or more alcohols comprises methanol.

17. The process of claim 1 wherein the ratio of the volume of the alcohol added or, when more than one alcohol is added, the total volume of alcohol added to the volume of solvent is from about 1:1 to about 1:2.

18. The process of claim 1 wherein said compound of Formula I is isolated by filtration and said isolated compound of Formula I has a purity of greater than about 95%.

19. The process of claim 1 wherein said compound of Formula I is isolated by filtration in a yield greater than about 70% by weight based on the amount of said compound of Formula II.

20. The process of claim 1 wherein said compound of Formula I is isolated by filtration in a yield greater than about 70% by weight based on said compound of Formula II and with a purity of greater than about 95% without the use of additional distillation, extraction, or chromatographic techniques.

21. The process of claim 14, wherein the ratio of the volume of the alcohol added or, when more than one alcohol is added, the total volume of alcohol added to the volume of solvent is from about 1:1 to about 1:2.

22. The process of claim 21 wherein:
said alcohol comprises methanol, ethanol, isopropanol, or a combination thereof; said solvent is toluene; R is hydrogen; $R_1$ is hydrogen; $R_2$ is propynyl; each $R_3$ is 2-propyl; and each Ar is phenyl.

* * * * *